United States Patent [19]

McFarlane

[11] Patent Number: 4,710,173

[45] Date of Patent: Dec. 1, 1987

[54] FLASHBACK STRUCTURE

[76] Inventor: Richard H. McFarlane, 2571 Kaneville Rd., Geneva, Ill. 60134

[21] Appl. No.: 843,493

[22] Filed: Mar. 24, 1986

[51] Int. Cl.[4] ............................................. A61M 5/00
[52] U.S. Cl. .................................... 604/168; 604/900
[58] Field of Search ................. 604/168, 52, 53, 900, 604/169

[56] References Cited

U.S. PATENT DOCUMENTS 4,269,186 5/1981 Loveless et al. ..................... 604/168
4,365,630 12/1982 McFarlane ........................... 604/168
4,525,157 6/1985 Vaillancourt ........................ 604/168

*Primary Examiner*—Stephen C. Pellegrino
*Attorney, Agent, or Firm*—John Cyril Malloy

[57] ABSTRACT

A flashback structure of the type primarily designed to be used in combination with a catheter assembly and more specifically structured to provide clear visual indication of blood flow along a circuitous path of fluid flow which is indicative of proper placement of the sharpened tip of a needle in a blood vessel wherein the catheter assembly can then be removed from the supporting needle or cannula and enter the vessel.

15 Claims, 7 Drawing Figures

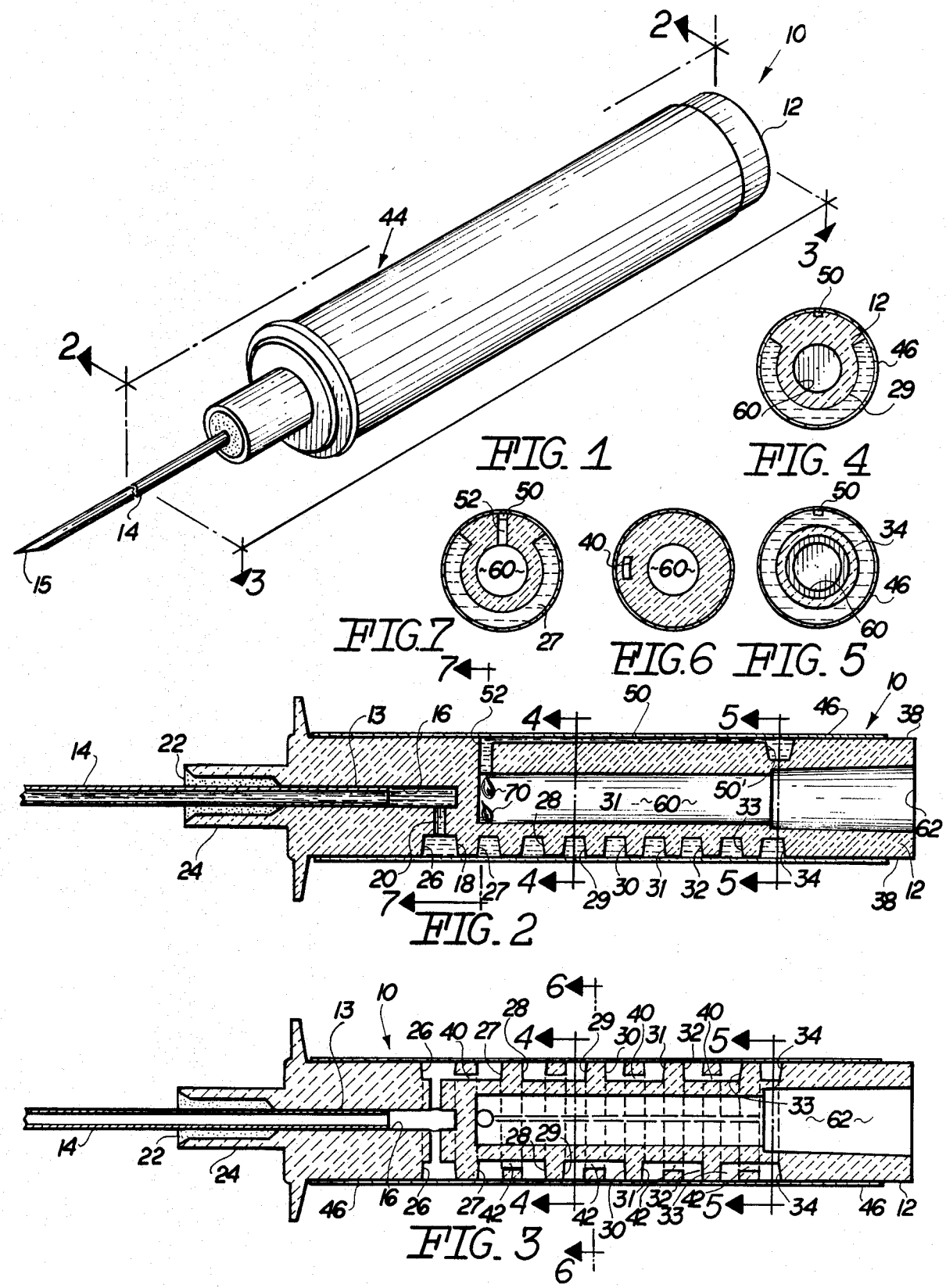

FLASHBACK STRUCTURE

BACKGROUND OF THE INVENTION

1. Field of the Invention

This invention relates to a flashback structure of the type formed specifically on the base member attached to a proximal end of a hollow needle having a sharpened tip at the distal end thereof and further wherein the base and needle structure are primarily designed for the support and placement of a catheter assembly properly within a blood vessel. A fluid flow channel is formed in a circuitous configuration on the base and disposed and structured for visual observation of blood entry and travel along the flow channel wherein such proper flow is indicative of proper placement of the sharpened tip within the blood vessel, the latter being necessary for positioning of the catheter in the same blood vessel.

2. Description of the Prior Art

In the utilization of a catheter assembly to the extent of proper placement of the catheter assembly, the sharpened tip of the supporting needle or cannula on which the catheter structure is mounted first penetrates the designated blood vessel. When the sharpened tip is properly positioned, blood flows continuously through the hollow support needle from the tip to a proximal end thereof which is fixedly attached to a gripping base. The blood passing from the blood vessel through the needle will continue to flow into any receiving chamber or cavity. Such flow characteristics allows the medical personnel applying the catheter to visually observe the blood flow. If the flow is continuous, the user knows that the tip of the needle is properly positioned in a vein or artery and the catheter, coaxially disposed about the penetrating needle is ready for subsequent advancement into the vein or artery in which the needle tip has been properly positioned.

Visual observation of incoming blood flow is recognized as an efficient and proper means of determining whether the sharpened tip of a needle is positioned within the blood vessel of the patient. There is a need in the medical profession for what may be termed a flashback structure which is specifically designed to enhance or facilitate the visual observation of blood flow from the needle into the base or gripping portion of the catheter assembly. Such a flashback structure ideally should be capable of providing observation, not only of the initial start of blood flow, but the determination that the incoming blood is in a state of continuous flow as the blood passes from the proximal end of the catheter into the flashback structure. For example, in such instances where the sharpened tip passes completely through the blood vessel, there will be an initial flow of blood passing through the needle and into the leading end of the flashback structure or chamber. However, if the path of fluid flow of the blood entering the flashback chamber or cavity is not properly designed, visual observation to determine whether the blood flow is initial or continual may be difficult.

In the prior art, U.S. Pat. No. 4,365,630 to McFarlane discloses a flashback chamber providing a substantially circuitous path of blood flow as it enters the base of the flashback chamber. While efficient and operable for its intended function, the structure disclosed in the above noted patent may also be somewhat difficult and/or expensive to produce due to the relatively complex structure in forming the preferred circuitous path of blood flow used to enhance visual observation thereof.

The present invention relates to a flashback structure of a simplified design and construction yet which may facilitate visual observation of blood flow to the extent that determination of continuous blood flow is readily accomplished.

SUMMARY OF THE INVENTION

The flashback structure of the present invention is, as generally set forth above, designed for use primarily in combination with a catheter assembly. The referred to catheter assembly is not specifically shown, for purposes of clarity, but is of the type including a catheter hub disposed in coaxial, jacketed and slidable relation about a hollow needle. The referred to needle has a distal end or tip which is sharpened to facilitate penetration and entry of the needle into the blood vessel of the patient. The proximal end of the needle is mounted on the interior of a base portion and, due to the fact that the needle is hollow along its entire length, blood flow, after entry of the sharpened tip into the blood vessel, occurs along the full length of the needle into the interior of the base as it flows from the proximal end secured to the base.

A flow channel is formed on the base and is structured to define a path of fluid flow of the blood passing from the proximal end of the hollow needle. More specifically, the path of fluid flow is specifically designed to have a circuitous configuration thereby facilitating visual observance of the movement or passage of the blood along the length of the flow channel.

An important feature of the present invention is the provision of the flow channel being defined by a groove structure formed in the outer surface of the base and being dimensioned to extend into the base a sufficient depth to facilitate free flow of the blood along substantially the entire length of the flow channel as it leaves the proximal end of the needle. In order to accomplish the aforementioned circuitous path, the groove structure preferably comprises a plurality of groove segments disposed in substantially transverse relation to the length of the base and in at least partially surrounding relation thereto as each of the groove segments are disposed in spaced apart relation in the cylindrically configured exterior surface of the base.

A vent means is formed in direct fluid communication with the flow channel so that air being forced from the flow channel as blood enters can readily pass from the base to the exterior thereof. Again, in a preferred embodiment of the present invention to be described in greater detail hereinafter, the vent means comprises a vent groove also formed in the exterior surface of the base but being of a significantly lesser depth than any of the groove segments. The dimension or depth of the groove in the external surface of the base is sufficient to allow free passage or flow of air therealong to a vent port which exits to the exterior of the body or atmosphere. However, the depth or dimension of the vent groove is such as to allow but substantailly restrict blood or liquid flow therealong in order to hamper or delay the time required for the blood to reach the aforementioned vent port and pass into a hollow interior of the base which is exposed to the exterior and the surrounding atmosphere. Obviously, it would be a disadvantage if blood were to flow freely from the base or "leak" therefrom. Accordingly, the flow of blood is restricted, as it travels along the length of the vent groove, serving to lengthen the time of travel thereby encouraging hardening or coagulation of the blood and minimizing the amount of blood, if any, which actually exits the base.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is an isometric view of the flashback structure of the present invention with the hollow needle secured thereto but absent any catheter structure normally associated therewith.

FIG. 2 is a sectional view along line 2—2 of FIG. 1.
FIG. 3 is a sectional view along line 3—3 of FIG. 1.
FIG. 4 is a sectional view along line 4—4 of FIG. 2.
FIG. 5 is a sectional view along line 5—5 of FIG. 2.
FIG. 6 is a sectional view along line 6—6 of FIG. 3.
FIG. 7 is a sectional view along line 7—7 of FIG. 2.

Like reference numerals refer to like parts throughout the several views of the drawings.

DETAILED DESCRIPTION OF THE PREFERRED EMBODIMENT

As shown in FIGS. 1, 2 and 3, the flashback structure of the general invention is generally indicated as 10 and includes a base 12 which is preferably formed from a rigid material and which is fixedly secured to an elongated hollow needle 14 having a proximal end secured within base 12 as at 13. The proximal end 13 is disposed in fluid communication with a receiving channel 16 for the directing of fluid flow, such as inflowing blood, into the body 12 and more specifically, into the beginning of a flow channel as at 18 through a connecting port 20.

The opposite or distal end of needle 14 has a sharpened tip 15 to facilitate penetration and entry of the tip into a designated blood vessel of the patient. Once so positioned and as pointed out above, proper entry and positioning of the tip 15 into the blood vessel establishes a continuous flow of blood through the sharpened tip 15, along the length of the needle 14, and out of the proximal end 13 into the receiving channel 16. Proper securement of proximal end 13 of needle 14 in the position shown in FIGS. 2 and 3 is insured due to the provision of an adhesive collection 22 disposed in surrounding and interconnecting relation between outstanding nose or finger portion 24 at the leading end of the base 12 and the exterior surface of the needle 14.

An important feature of the present invention is the provision and structure of the flow channel. The flow channel comprises a groove structure which preferably includes a plurality of groove segments 26 through 34 (actual number may vary), each having a curvilinear or semi-circular, arcuate configuration. Each of the groove segments are integrally formed in the exterior, cylindrical surface 38 of the base 12, the configuration of which may be termed a substantially barrel type configuration.

It should be noticed that though the plurality of groove segments 26 through 34 collectively extend along the length of the base 12, each groove extends in at least partially surrounding relation to the longitudinal axis of the base 12 due to its curvilinear or semi-circular configuration (see FIGS. 2 and 3).

Further with reference to FIG. 3, a circuitous path of travel of incoming blood is defined as it flows along the length of the flow channel 25 in that adjacently positioned pairs of groove segments are interconnected in fluid communication with one another by a plurality of connecting ports 40 interconnecting adjacent pairs of grooves 26, 27; 28, 29; 30, 31; and 32, 33 at one end of the adjacent pairs as set forth above. In addition, a plurality of connecting ports 42 are located at the opposite end of additional adjacent groove segments 27, 28; 29, 30; 31, 32; and 33, 34 (see FIG. 3). Therefore, it is readily apparent, that the direction of travel of the blood as it passes along the length of the flow channel 25 is successively reversed as it passes through the successive connecting ports 40 and 42 at opposite ends of the grooves 26 through 34. A circuitous path of fluid flow is thereby established as the blood travels along the length of flow channel 25. In order to retain fluid flow throughout the flow channel 25 generally and particularly through the plurality of groove segments 26 through 34. A cover means generally indicated as 44 is provided in the form of an elongated sleeve open at both ends and positioned in surrounding relation to the exterior, cylindrical surface of the base 12. In a preferred embodiment, the sleeve 46 is formed from an at least partially transparent material capable of being heat shrunk and thereby permanently affixed to the exterior cylindrical surface 38 in covering relation to each of the groove segments 26 through 34 and vent groove 50. As clearly shown in FIGS. 2 and 3, the covering disposition of the sleeve 46 relative to the open end of the groove segments serves to retain fluid so that fluid flow is established along the length of the flow channel.

It is apparent that as the blood enters the flow channel and successively passes therethrough each of the groove segments 26 through 34, air, previously occupying such space, must be vented. Accordingly, the present invention includes a vent means including an elongated vent groove 50 also formed in the exterior cylindrical surface 38 but being of a substantially reduced thickness or depth into the interior body 38. The reduced depth of vent channel 50 establishes a sufficient cross sectional dimension of the vent groove 50 to allow air to flow therethrough and exit from a vent port 52 located at one end of the vent groove 50. The opposite end of the vent groove 50 as at 50' is disposed in direct fluid receiving relation to the endmost groove segment 34. Groove segment 34 differs in configuration from the remainder of the groove segments 26 through 33 in that it completely surrounds the exterior cylindrical surface 38 in an annular configuration as shown in FIG. 5.

The vent means further comprises the vent port 52 disposed in fluid communication with an interior cavity 60 extending into the hollow interior of the base 12 and having an open end 62 which communicates with the exterior of the base 12 so as to pass any vented air leaving vent port 52 into cavity 60 to atmosphere.

As set forth above, the substantially lesser depth of vent groove 50 into the surface 38 allows free air flow but restricts liquid flow. Accordingly, while the flow of blood through the flow chamber 25 will take a relatively short amount of time during a continuous blood flow condition, the passage of blood along the vent groove 50 will take a comparatively longer amount of time. This is to restrict or prevent blood passing through the vent port 52 and actually exiting into the central cavity 60 such as at 70. If a minimal amount of blood in fact reaches the hollow interior cavity 60, such blood will quickly coagulate or alternately, take such a long time that use of the base 12 and needle 14 will be ended since the catheter (not shown) will already be in place within the designated blood vessel.

Again, for purposes of clarity, the actual catheter structure is not shown, but such catheter structure would include an enlarged hub portion designed to fit over the nose or outstanding finger 24 and a tapered elongated hollow interior tube portion concentrically disposed in surrounding relation about the exterior of elongated needle 14.

It will thus be seen that the important features of the present invention made apparent from the preceding description are efficiently attained and since certain changes may be made in the above construction without departing from the scope of the invention, it is intended that all matter contained in the above description or shown in the accompanying drawings, shall be interpreted as illustrative and not in a limiting sense.

Now that the invention has been described,
What is claimed is:

1. A flashback structure of the type used to determine proper placement of a needle tip within a blood vessel, such as when placement of a catheter assembly within the blood vessel is being attempted, said structure comprising:
   (a) a base having an elongated configuration and an outer surface comprising a substantially elongated cylindrical configuration and including a needle extending outwardly from one end of said base, said needle terminating in a sharpened tip at a distal end thereof,
   (b) said needle comprising a hollow interior portion extending along the length thereof from said tip to a proximal end of said needle, said proximal end secured on the interior of said base, whereby blood travels along said needle into said base when said tip is located within said blood vessel,
   (c) a flow channel integrally formed on said outer cylindrical surface of said base and disposed in fluid communication with said needle at substantially one end of said base and a vent means at the opposite end of said flow channel relative to said needle,
   (d) said vent means formed on said cylindrical outer surface of said base for the exiting of air from said flow channel as blood enters therein from said needle,
   (e) said flow channel comprising a groove structure extending along at least a portion of the length of said base and comprising a plurality of groove segments,
   (f) said plurality of groove segments integrally formed in said cylindrical outer surface in spaced relation to one another and collectively extending between and in fluid communication with said proximal end of said needle and said vent means,
   (g) each of said groove segments comprising a curvilinear configuration disposed transversely to the length of said base in at least partially surrounding relation thereto and extending into said base a sufficient depth to allow a free flow of blood therealong, and
   (h) cover means being at least partially transparent and mounted in engaging and surrounding relation to said cylindrical outer surface of said base and in covering, fluid retaining relation to said plurality of groove segments and said vent means,
   (i) whereby blood is viewable as it flows from said needle along the length of said flow channel beneath said cover means when said tip is properly positioned within a blood vessel.

2. An assembly as in claim 1 wherein said cover means comprises a sleeve dimensioned and configured for concentric, mating engagement about said cylindrical outer surface and further disposed in covering relation to said base at least along the length of said flow channel.

3. A flashback structure as in claim 1 wherein said groove structure and said plurality of groove segments are disposed to define a circuitous path of travel for said blood entering said flow channel and passing from said needle to said vent means.

4. A flashback structure as in claim 2 wherein said sleeve is formed of a flexible, heat shrinkable material fixedly secured to said outer surface.

5. A flashback structure as in claim 1 wherein said vent means comprises a vent channel formed in said outer surface and connected at one end in fluid communicating relation with said flow channel and at the other end in fluid communication relation with the exterior of said body.

6. A flashback structure as in claim 5 wherein said vent channel is defined in part by a vent groove integrally formed in said outer surface and extending into said body a depth sufficient to allow flow of air and a restricted flow of blood therealong.

7. A flashback structure as in claim 6 wherein said depth of said vent groove is of a limited depth sufficient to restrict the rate of liquid flow therealong from said flow channel towards an exterior of said base.

8. A flashback structure as in claim 7 wherein said vent groove is formed to have a substantially lesser depth than said plurality of groove segements.

9. A flashback structure as in claim 1 wherein said groove structure further comprises a plurality of connecting ports each interconnecting adjacently positioned groove segments and interconnecting ports defining a continuous path of fluid flow along the length of said flow channel.

10. A flashback structure as in claim 9 wherein each of said connecting ports are disposed at opposite ends of alternately positioned groove segment pairs, said path of fluid flow defining successive reverse directions of travel along the length of said successively disposed groove segments, whereby observation of blood flow into and along the length of said flow channel is facilitated.

11. A flashback structure as in claim 9 wherein said vent means comprises a vent groove formed in said outer surface in spaced relation to a major length of said flow channel and extending into said base at a substantially reduced depth relative to a depth of said groove segments, said reduced depth being sufficiently dimensioned to allow flow of blood therealong and restrict the rate of such flow, said vent groove extending from an endmost groove segment along a length of said base to a vent port formed in said base and communicating with the exterior of said base.

12. A flashback structure as in claim 11 wherein said bass comprises a hollow interior communicating with the exterior of said base and in fluid communication with said vent port, air passing along said vent means to atmosphere through said hollow interior, said vent groove dimensioned for restricted blood flow therealong from said endmost groove segment to said vent port.

13. A flashback structure as in claim 12 wherein said cover means comprises a cover sleeve secured to said exterior cylindrical surface in covering, fluid retaining relation to said groove segments and said vent groove.

14. A flashback structure of the type used to determine proper placement of a needle tip within a blood vessel, such as when placement of a catheter assembly within the blood vessel is being attempted, said structure comprising:
  (a) a base having an elongated configuration and an outer surface comprising a substantially elongated cylindrical configuration and including a needle extending outwardly from one end of said base, said needle terminating in a sharpened tip at a distal end thereof,
  (b) said needle comprising a hollow interior portion extending along the length thereof from said tip to a proximal end of said needle, said proximal end secured on the interior of said base, whereby blood travels along said needle into said base when said tip is located within said blood vessel,
  (c) a flow channel integrally formed on said outer cylindrical surface of said base and disposed in fluid communication with said needle at substantially one end of said base and a vent means at the opposite end of said flow channel relative to said needle,
  (d) said vent means formed on said cylindrical outer surface of said base for the exiting of air from said flow channel as blood enters therein from said needle,
  (e) said flow channel comprising a groove structure extending along at least a portion of the length thereof between and in fluid communication with said proximal end of said needle and said vent means,
  (f) said groove structure extending into said outer surface a sufficient depth to allow a free flow of blood therealong from said needle to said vent means,
  (g) said vent means comprising a vent groove integrally formed in said outer surface and extending into said base a depth sufficient to allow flow of air and a restricted flow of blood therealong, and
  (h) cover means being at least partially transparent and mounted in engaging and surrounding relation to said outer surface of said base and in covering, fluid retaining relation to said plurality of groove segments and said vent groove,
  (i) whereby blood is viewable as it flows from said needle along the length of said flow channel and said vent groove beneath said cover means when said tip is properly positioned within a blood vessel.

15. A flashback structure as in claim 14 wherein said vent groove is formed in said outer surface in spaced relation to a major length of said flow channel and being at a substantially reduced depth relative to a depth of said groove structure, said reduced depth being sufficiently dimensioned to allow flow of blood therealong and restrict the rate of such flow, said vent groove extending from an endmost portion of said groove structure along a length of said body to a vent port formed in said body and communicating with the exterior of said body.

* * * * *